United States Patent [19]

Helfgott et al.

[11] 4,324,243

[45] Apr. 13, 1982

[54] APPARATUS AND PROCESS FOR ASPIRATING AND EVACUATING A SURGICAL SITE

[76] Inventors: Maxwell A. Helfgott, 5640 Bradley Blvd., Bethesda, Md. 20014; Gerald N. Helfgott, 5513 Uppingham St., Chevy Chase, Md. 20015

[21] Appl. No.: 97,983

[22] Filed: Nov. 28, 1979

[51] Int. Cl.³ .............................................. A61M 1/00
[52] U.S. Cl. ...................................... 128/276; 433/95
[58] Field of Search ............... 128/276, 277, 278, 297, 128/303 R; 251/7; 137/205; 433/92, 95

[56] References Cited

U.S. PATENT DOCUMENTS

| | | | |
|---|---|---|---|
| 3,542,031 | 11/1970 | Taylor | 128/276 |
| 3,568,318 | 3/1971 | Martin | 433/100 |
| 3,812,855 | 5/1974 | Banko | 128/276 |
| 3,815,604 | 6/1974 | O'Malley | 128/305 |
| 3,884,237 | 5/1975 | O'Malley et al. | 128/303.14 |
| 3,884,238 | 5/1975 | O'Malley et al. | 128/305 |
| 3,920,014 | 11/1975 | Banko | 128/230 |
| 3,932,065 | 1/1976 | Ginsberg et al. | 128/276 |
| 4,007,742 | 2/1977 | Banko | 128/230 |
| 4,019,514 | 4/1977 | Banko | 128/230 |
| 4,117,843 | 10/1978 | Banko | 128/230 |
| 4,168,707 | 9/1979 | Douvas | 128/276 |
| 4,176,671 | 12/1979 | Citrin | 137/1 |
| 4,274,411 | 6/1981 | Potson, Jr. | 128/276 |

FOREIGN PATENT DOCUMENTS 2758909  9/1978  Fed. Rep. of Germany ...... 128/276

OTHER PUBLICATIONS

"Expermental Vitrectomy" Peyman et al., Arch Ophthal, vol. 86, Nov. 1971, pp. 548-551.
"Surgical Procedures Publication", The Ocutome Newsletter, vol. 2 No. 2, Jun. 1977 San Leandro Calif. pp. 1-5.
"Lovac Power Drain" Cat. Cut Toledo, Ohio, 1929.

Primary Examiner—Robert W. Michell
Assistant Examiner—J. L. Kruter
Attorney, Agent, or Firm—Irons and Sears

[57] ABSTRACT

An apparatus and process for aspirating and evacuating a pneumatically operated surgical instrument, such as an intraocular vitrectomy unit having a reciprocating blade for severing unwanted intraocular tissues, is disclosed herein. The apparatus includes a collapsible conduit pneumatically connected to a receptacle for conducting an aspirating negative pressure to the surgical instrument and evacuating material received therefrom into the receptacle. A pneumatically operated clamping means functions both to terminate the application of negative pressure through the collapsible conduit and to eliminate residual negative pressure within the conduit between the blocked portion of the conduit and the surgical instrument. Positive coordination between the pneumatically powered surgical intrument and the aspiration and evacuation system is achieved by fluidly connecting both the instrument and the clamping means to the same power output, so that the aspiration and evacuation commences as the reciprocating blade of the surgical instrument cuts and ceases as the blade withdraws.

10 Claims, 5 Drawing Figures

APPARATUS AND PROCESS FOR ASPIRATING AND EVACUATING A SURGICAL SITE

BACKGROUND OF THE INVENTION

This invention relates to aspiration and evacuation systems for surgical instruments, such as intraocular vitrectomy units. The invention is particularly useful as an aspirating and evacuating system for the pneumatic intraocular surgical handpiece disclosed in copending U.S. patent application Ser. No. 097,984, filed on even date herewith, invented by Maxwell D. Helfgott, M.D. and Gerald N. Helfgott, and entitled "Powered Handpiece For Endophthalmic Surgery".

Before one may appreciate all the features of the aspirating and evacuating system described herein, one must first have some understanding of the surgical instruments such systems are commonly applied to. One such surgical instrument is the intraocular vitrectomy unit used for removing vitreous tissue within the eyes of humans or animals.

Intraocular vitrectomy units are basically comprised of a handpiece including a short, elongated cutting tube mounted onto a handle. The cutting tube is operated by a pneumatic or electric power source connected to the handle of the unit. In some ways, the cutting tube is structurally similar to a needle valve used to pump air into athletic equipment such as footballs and basketballs. Like a needle valve, the cutting tube is hollow throughout its interior, closed on its distal end, and has a small lateral port near its end for transmitting a pneumatic pressure. However, unlike a needle valve, the cutting tube has either a rotating or reciprocating blade member located within its hollow interior. Further, the lateral port transmits a negative, rather than a positive pneumatic pressure.

During an operation, the cutting tube of the vitrectomy unit is inserted through the wall of the eyeball and into the vitreous tissue and fluids contained therein. An aspirating and evacuating unit is fluidly connected to the hollow interior of the cutting tube, and the lateral port of the tube is manipulated so that a segment of unwanted intraocular tissue is drawn into the port by the negative aspirating pressure, along with some of the vitreous fluids contained within the eyeball. The rotary or reciprocating blade member severs into discrete chunks the tissue drawn into its lateral port by rhythmically shearing it between the edge of the port and the rotating or reciprocating blade. The negative aspirating pressure continues to act on these discrete chunks of tissue and vitreous fluids and withdraws them through the hollow interior of the cutting tube and out of the vitrectomy unit by means of an evacuation conduit.

In addition to aspirating and evacuating systems, intraocular vitrectomy units usually also include irrigation systems which prevent the eyeball from collapsing due to the evacuation of tissue and fluids therefrom. Such irrigation systems positively inject fluid into the interior of the eyeball as the aspirating and evacuating units suck fluids and tissue out of the eye. This way, the net fluid pressure within the eyeball is maintained at the normal level above atmospheric pressure, and all eye components remain in their approximate normal positions during the operation of the vitrectomy unit.

Ideally, an aspirating and evacuating unit for use with a surgical vitrectomy unit should provide a source of aspirating or suction pressure which is easily and accurately controllable in order to minimize the danger of accidentally destroying delicate tissues, such as the retina within the eye. Specifically, the unit should provide a source of suction with "digital" cut off characteristics (i.e., the ability to cut off immediately with respect to time like a square wave function, rather than trailing off gradually with time like an inverse ramp function). Furthermore, the action of the aspirating and evacuating unit should be positively and directly coordinated with the action of the blade of the vitrectomy unit, so that the suction pressure is actuated only during the cutting stroke of the reciprocating blade. Consistent with the preceding requirements, the unit should have suction controls which possess an extremely high degree of mechanical reliability. Such a unit should also be simple in construction in order to facilitate both mass production and reliability. Finally, it would be desirable if such a unit were compatible with a variety of prior art vitrectomy units, rather than just one special type of vitrectomy unit.

Aspirating and evacuating systems for intraocular vitrectomy units are known in the prior art. Examples of such systems are disclosed in U.S. Pat. Nos. 3,812,855, 3,884,237, 3,884,238, 3,920,014, 4,007,742, 4,019,514, and 4,117,843. However, each of the prior art systems disclosed in these patents falls short of fullfilling at least one of the aforementioned ideal criteria.

For example, the suction controller disclosed in U.S. Pat. No. 3,812,855 coordinates the coaction between its pneumatically operated vitrectomy unit and its suction and evacuation system through an electrical interfacing in the form of electrically operated valves. Additionally, the structure of this invention is intricate, utilizing many moving parts. The use of an indirect electrical coordination system in such a complicated device instead of a direct, pneumatic coordination system in a relatively simple device makes simultaneous coaction between the blade and suction unit mechanically more difficult to attain, and increases the chance of equipment malfunction. Finally, this particular invention utilizes flexible tubing between the vitrectomy and the source of suction, and makes no provision for dealing with the residual negative pressure trapped between the suction cut off valves and the vitrectomy unit. Thus a "digital" cut-off of suction pressure is difficult, if not impossible.

The aspiration and evacuation systems disclosed in U.S. Pat. Nos. 3,815,604, 3,884,237 and 3,884,238 also utilize an electrical infacing in the form of a solenoid operated, rotary gate valve for coordinating simultaneous coaction between the suction unit and the vitrectomy unit. Further, no provision is made for eliminating residual negative pressure trapped between the suction tube and the vitrectomy unit. Thus a "digital" cut off of suction pressure is again difficult or impossible. Moreover, the structure of the vacuum control of this invention is complicated by the fact that the suction source functions to reciprocate the blade of the vitrectomy unit as well as to power the aspiration and evacuation system.

Finally, the aspiration and evacuation systems disclosed in U.S. Pat. Nos. 3,920,014, 4,007,772, 4,019,514 and 4,117,843 again utilize an electrical interface to control the coaction of their respective blade units and aspiration and evacuation units. While the aspiration control in each of these inventions recognizes the problems associated with residual negative pressure existing in the suction line between the suction unit and the vitrectomy unit after the suction unit is stopped, the solutions proposed in these patents are very difficult to apply. For example, the 3,920,014 patent suggests reversing the peristaltic suction pump to minimize the residual pressure, or opening the clamping mechanism of the peristaltic pump so that the evacuation line is effectively vented. Either of these solutions would require precisely timed execution in order to effectuate a "digital", essentially instantaneous cut off of the negative aspirating pressure.

The shortcomings of the preceding representative samples of the prior art clearly illustrate the need for an aspiration and evacuation unit capable of directly coacting with a vitrectomy blade unit without a complicated electropneumatic interface, and further capable of selectively and digitally cutting off the negative pressure of aspiration to avoid damaging delicate tissue.

SUMMARY OF THE INVENTION

The invention encompasses both an apparatus and a process for aspirating and evacuating material from a pneumatically powered surgical instrument without any of the aforementioned shortcomings associated with the prior art.

Basically, the invention includes a receptacle for receiving material evacuated from a pneumatically powdered surgical instrument. This receptacle in turn includes both a pneumatic connection means for pneumatically connecting the interior of the receptacle to a source of negative pressure, and an adjustable pressure valve for adjusting and maintaining a negative pressure contained within the receptacle when the pneumatic connecting means is connected to a negative pressure source. A collapsible conduit pneumatically connects the surgical instrument with the interior of this receptacle and evacuates material out of the surgical instrument and into the receptacle. A pneumatically actuated clamping means serves both to terminate the application of negative pressure through the collapsible conduit to the surgical instrument, and to eliminate residual negative pressure in the conduit between the clamp and the instrument, by clamping a section of the conduit. Finally, a pneumatic "T" or "Y" connection fluidly connects both the clamping means and the surgical instrument to the pneumatic power output line of a pneumatic control unit so that negative pressure is applied only during the cutting stroke of the blade of the surgical instrument.

This "T" or "Y" connection between the power output line and the clamping means and surgical instrument effectuates a positive, direct coaction between the negative aspirating pressure and the reciprocating blade of the surgical instrument and obviates the need for the indirect and complicated electrical systems used in the prior art to approximate simultaneous coaction between the blade of the instrument and the aspiration system.

Furthermore, the use of a clamping means to cut off the negative pressure applied through the aspiration conduit, rather than the gate valves or spool valves predominantly used in the prior art, serves to eliminate residual suction in the collapsible conduit when the aspiration and evacuation system is cut off by reducing the interior volume of the conduit in the section between the clamping means and the instrument.

Finally, the unit is simple in construction and hence easily and inexpensively mass produced, and compatible with a variety of prior art vitrectomy units.

DETAILED DESCRIPTION OF THE PREFERRED EMBODIMENT

Figure 1:
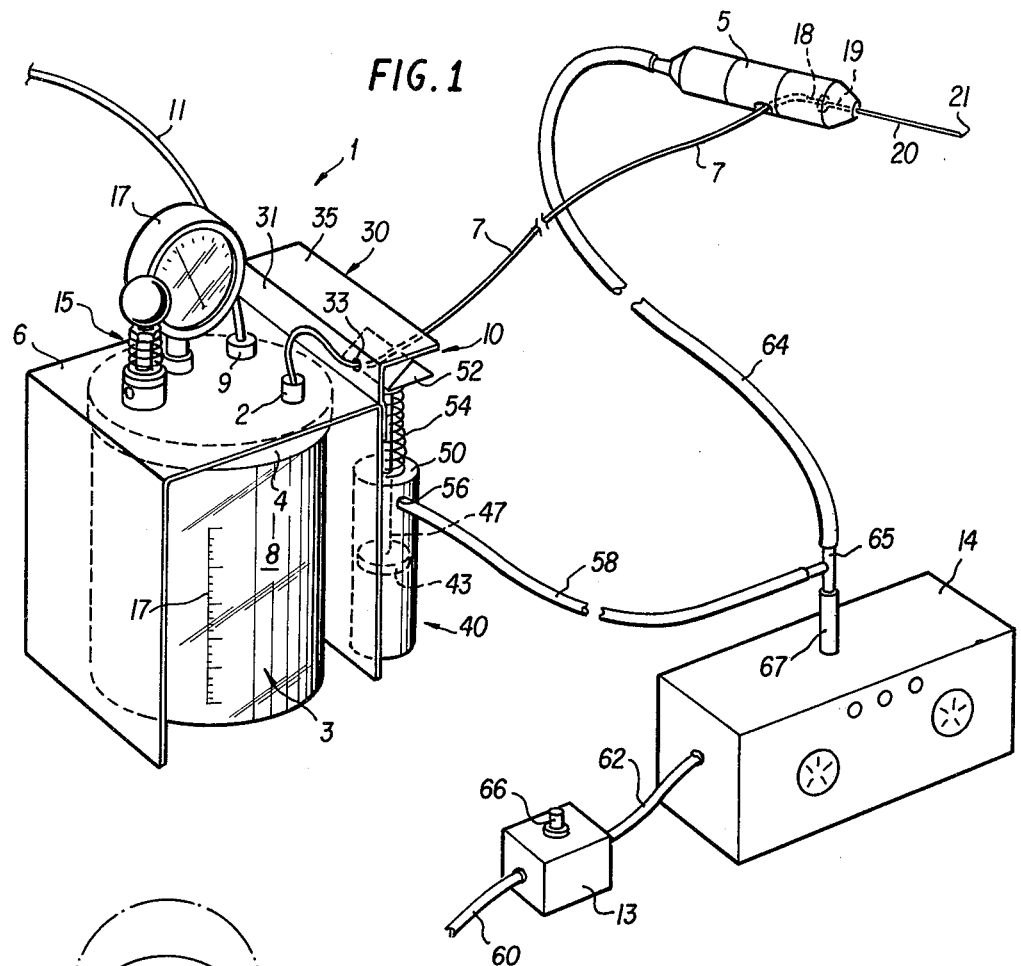
FIG. 1 is a perspective view of the preferred embodiment of the aspiration and evacuation system of the invention as used with a pneumatically operated surgical instrument.

With reference to FIG. 1, the aspiration and evacuation apparatus 1 of the invention generally comprises a receptacle 3 for receiving material evacuated from the surgical instrument 5, a flexible, collapsible conduit 7 for conducting a negative pressure from the receptacle 3 to the surgical instrument 5, a clamping assembly 10 for cutting on or off the flow of negative pressure in conduit 7 by clamping or unclamping a section of the conduit, respectively, and a pneumatic connection means 65 for fluidly connecting both the surgical instrument 5 and the clamping means 10 to the power output line 67 of a pneumatic control unit 14 and thereby coordinating the action of the surgical instrument and the aspiration and evacuation apparatus.

Figure 2:
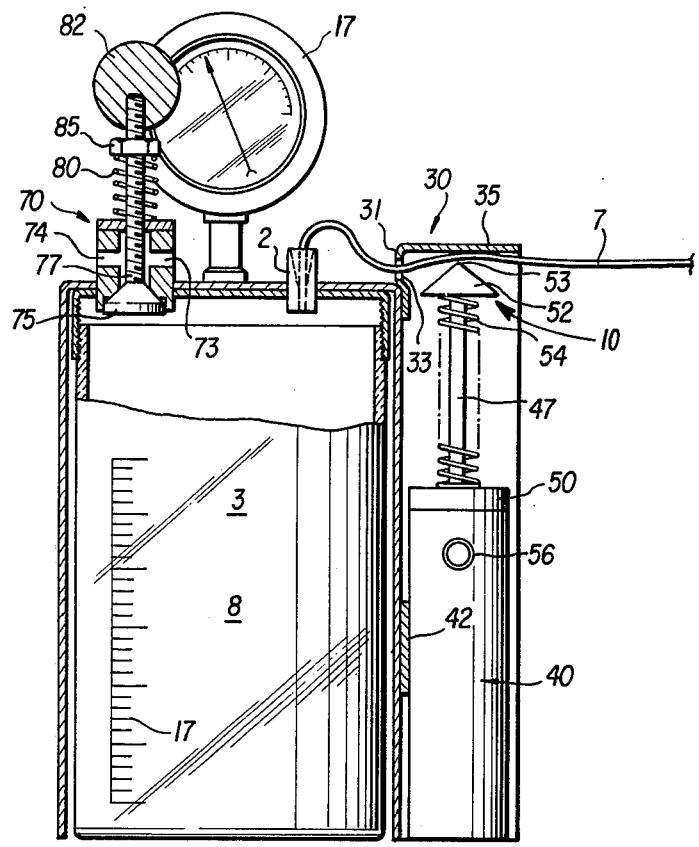
FIG. 2 is a partial cross sectional view of the preferred embodiment of the invention.
Figure 5:
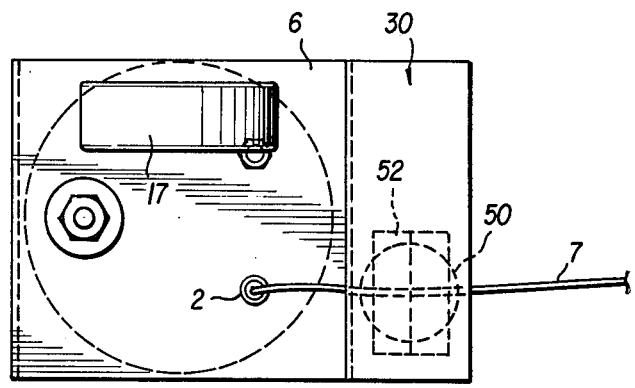
FIG. 5 is an elevational view of the preferred embodiment of the invention.

With reference now to FIGS. 1 and 2, the receptacle 3 of the preferred embodiment includes a screw type lid 4 which is screwed onto a transparent glass body 8 having a series of graduations 17 so that the total amount of material evacuated into receptacle 3 from the surgical instrument 5 may be easily determined. Screw type lid 4 of the receptacle 3 includes a bracket 6 for mounting clamping means 10. Bracket 6 is preferably formed from sheet metal. The lid 4 of receptacle 3 also includes a conventional pneumatic connector 9 for pneumatically connecting the interior of the receptacle 3 to a source of negative pressure (not shown) via pneumatic line 11. Further, lid 4 of receptacle 3 includes an adjustable pressure valve 15 for adjusting and maintaining a selected negative pressure within the interior of the recepticle. Additionally, a vacuum gauge 17 is pneumatically and mechanically connected to the lid 4 of receptacle 3 as shown for adjusting and monitoring the value of the negative pressure present in the interior of the receptacle. Finally, lid 4 of receptacle 3 also includes a fluid connection 2 for fluidly connecting collapsible conduit 7 to the interior of the receptacle.

Collapsible conduit 7 functions both to conduct negative aspirating pressure from the interior of receptacle 3 to the surgical instrument 5, and to evacuate material out of the instrument 5 into the interior of receptacle 3. Surgical instrument 5 may be a pneumatically controlled, intraocular vitrectomy unit, and is preferably the vitrectomy unit disclosed in the previously referred to copending patent application Ser. No. 097,984, filed on even date herewith, the specification of which is expressly incorporated herein by reference. In such vitrectomy units, conduit 7 is fluidly connected to the proximal end 18 of a hollow open-ended inner tube 19 slidably received within the outer hollow cutting tube 20, and conducts an aspirating, negative pressure to a lateral port (not shown) located in the distal end 21 of the cutting tube 20.

The negative pressure applied through conduit 7 is cut on or off by the clamping assembly 10. Clamping assembly 10 includes a bracket 30 mounted on bracket 6 as shown and having a vertical portion 33 and a horizontal portion 35 which forms a clamping wall as hereinafter explained. Like bracket 6, bracket 30 is preferably fabricated out of sheet metal. The vertical portion 33 of the bracket 30 may be either tack welded or integrally formed with bracket 6 in the position shown. Vertical portion 33 includes an aperture 31 through which conduit 7 extends.

Clamping assembly 10 further includes a reverse acting piston 40 which is mounted onto one of the side walls of the bracket 6 by means of piston bracket 42. Reverse acting piston 40 is preferably a Clippard Corporation model 355-AR-1/2. With specific reference to FIG. 1, piston 40 includes a piston member 43 which is slidably movable within cylinder 45. Piston 40 further includes a piston rod 47 mechanically connected to piston member 43. Piston rod 47 extends through sealing ring 50 of cylinder 45 as shown. A clamping member 52 which is preferably prism shaped is connected to the distal end of the piston rod 47. Clamping member 52 is also preferably proportioned relative to the vertical portion 33 of bracket so that rotation within bracket 30 is impossible. This way, proper orientation of the clamping corner 53 of clamping member 52 relative to collapsible conduit 7 is maintained as member 52 reciprocates. Clamping member 52 is biased toward the clamping wall formed by the surface of bracket portion 35 by means of a spring 54 compressed between the upper surface of sealing ring 50 and lower surface of clamping member 50. Spring 54 is held in place by heliocentrically disposing it around the upper portion of piston rod 47 as shown. Cylinder 45 of piston 40 includes a pneumatic connector 56 onto which one end of pneumatic conduit 58 is connected. The other end of pneumatic conduit 58 is fluidly connected to pneumatic connection means 65, which fluidly connects the interior of cylinder 45 of piston 40 with the power output line 67 of pneumatic control unit 14. The pneumatic circuit formed by pneumatic conduit 58 and pneumatic connection means 65 causes piston member 40 to reciprocate within cylinder 45 in accordance with the pneumatic pulses generated by pneumatic control unit 14. Control unit 14 is connected to pneumatic power conduit 60 which may in turn be connected to a tank of pressurized nitrogen or carbon dioxide gas. A pneumatic switching means 13 is connected between pneumatic power conduit 60 and pneumatic control unit 14 for cutting pneumatic control unit 14 "on" or "off". Pneumatic switching means 13 includes an actuating button 66 which, when depressed, will open switch 13, and allow pressurized gas to flow into control unit 14.

Generally speaking, pneumatic control unit 14 is a variable pneumatic oscillator capable of generating a variety of pneumatic waveforms. The period of these waveforms determines the period of the reciprocation of the blade within cutting tube 21 of surgical instrument 5. Like clamping assembly 10, the pneumatically operated surgical instrument 5 is also fluidly connected to the power output line 67 of the pneumatic control unit 14 by way of pneumatic connection means 65. The fact that both the instrument 5 and the clamping assembly 10 are both fluidly connected to the power output line 67 of the control means 14 via connection means 65 insures a positive, direct coaction between the two, as will become more apparent hereafter.

Figure 3:
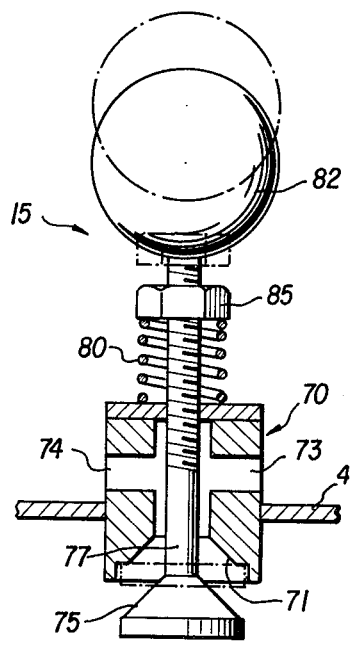
FIG. 3 is cross sectional view of the preferred adjustable pressure valve of the invention.

With reference now to FIG. 3, the pressure adjustment valve 15 includes a valve body 70 in air tight relationship with receptacle lid 4. Valve body 70 includes a valve seat 71 and a pair of vent ports 73, 74 located above lid 4 and bracket 6 as shown. Adjustment valve 15 further includes a frusto-conical valve member 75 having a valve stem 77. Valve stem 77 is threaded at its distal end to threadably receive nut 78. A spring 80 heliocentrically disposed around valve stem 77 between nut 78 and valve body 70 serves to bias the conical surface of valve member 75 against valve seat 71. Finally, pressure adjustment valve 15 includes a ball member threadably mounted onto the distal end of valve steam 77. Ball member 82 facilitates the manual depression of valve stem 77 to vent the interior of jar 3 through ports 73, 74 should that become necessary.

Figure 4:
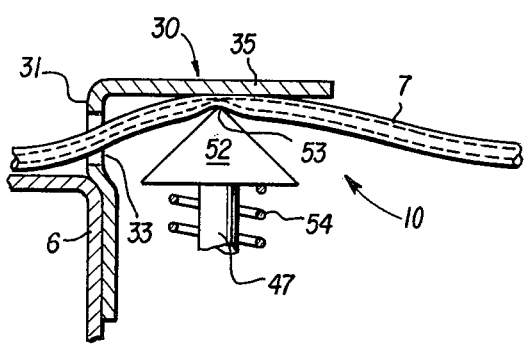
FIG. 4 is a cross sectional, detailed view of the preferred clamping means of the invention.

The operation of the invention may best be understood with reference to FIGS. 1, 2, and 4. Initially, pneumatic connection 9 is fluidly connected to a source of negative pressure via conduit 11, which may be a standard hospital suction outlet. Next, the value of the desired aspirating and evacuating pressure is selected by screwing nut 78 of adjustable pressure valve 15 either up or down, until the desired negative pressure registers on pressure gauge 17. At this point in time, collapsible aspirating and evacuating conduit 7 is clamped or pinched shut between the lower surface of horizontal portion 35 of bracket 30 and the orthogonal corner 53 of prism shaped clamping member 52 due to the biasing force of spring 54 pushing against the lower surface of the clamping member as shown.

When pneumatic switch 13 is opened by depressing button 66 either manually or by foot, pneumatic power line 60 is fluidly connected to pneumatic control unit 14, which generates a series of pneumatic pulses and transmits them through pneumatic output line 67. These pulses are simultaneously transmitted to both the piston 40 of clamping assembly 10 and the surgical instrument 5. Each of these pulses simultaneously causes the hollow open-ended inner tube 19 of instrument 5 to move toward the distal end of outer hollow cutting tube 20 in a cutting stroke. At the same time, each of these pulses exerts pressure against the upper surface of piston member 43 and causes piston member 43 to overcome the upward biasing force exerted by spring 54, and withdraws the orthogonal edge 53 of prism shaped clamping member 52 away from the aspirating and evacuating conduit 7 approximately into the position shown in FIG. 2. This in turn allows conduit 7 to conduct a negative pressure between receptacle 3 and surgical instrument 5 for aspiration purposes for the duration of the cutting stroke of inner tube 19.

At the end of each of the pneumatic pulses generated by control unit 14, the air inside the piston cylinder 45 of clamping assembly 10, and the air inside surgical instrument 5, escapes through pneumatic output line 67 by way of a vent (not shown) located in the control unit 14. This in turn causes spring 54 to forceably clamp aspiration and evacuation conduit 7 between the lower surface of bracket portion 35 and the orthogonal edge 53 of clamping member 52 into the position shown in FIG. 4. The contraction of the internal volume of conduit 7 in the vicinity of orthogonal edge 53 eliminates any residual suction that would be present in conduit 7 between surgical instrument 5 and clamping assembly 10 due to contraction of the collapsible conduit 7 caused by the negative pressure conducted within. Although the clamping member in the preferred embodiment is a prism shaped member having an orthogonal edge, the invention contemplates the use of a variety of clamping member shapes, and is not limited to this particlar geometry.

At the same time spring 54 is forceably clamping conduit 7 shut again, a small spring (not shown) in surgical instrument 5 returns the open-ended inner tube 19 of instrument 5 back toward the proximal end of instrument 5 in preparation for another cutting stroke. The cycle is repeated with each pneumatic pulse from control unit 14.

As previously stated, the invention encompasses a process for aspirating and evacuating a pneumatically surgical instrument, as well as an apparatus. The first step of this process may include fluidly connecting the interior of receptacle 3 with a source of negative pressure. The second step may include fluidly connecting the collapsible aspiration and evacuation conduit 7 to the receptacle 3 on one end and the surgical instrument 5 at the other end while clamping assembly 10 is clamped over a section of the conduit 7. The third step of the process may include fluidly connecting both the surgical instrument 5 and the clamping assembly 10 to the power output line 67 of a pneumatic control unit 14. The fourth step of the process may include simultaneously actuating the surgical instrument 5 and the clamping assembly 10 by fluidly connecting the pneumatic control unit 14 to a pneumatic power conduit 60.

Having described our invention in such full, clear and concise terms as to enable any person of ordinary skill in the surgical engineering art to make and use the same, we claim:

1. A surgical apparatus comprising:
   (a) a powered intraocular surgical instrument of the type which is actuated by a series of pneumatic pressure pulses;
   (b) a pneumatic control unit for providing a series of pneumatic pressure pulses to actuate said surgical instrument;
   (c) a collapsible conduit fluidly connecting said surgical instrument with a source of negative pressure for aspirating said instrument and evacuating material from said instrument;
   (d) a pneumatically operated clamping means which is effective when deactuated to cut off the application of negative pressure through said collapsible conduit by clamping a section of said conduit, and to contract the interior volume of said conduit between said clamping means and said instrument to dissipate residual negative pressure existing therebetween, and which is effective when actuated by a pneumatic pressure pulse to unclamp said section of said conduit and thereby to permit negative pressure to be applied through said conduit; and
   (e) a pneumatic connection means fluidly connecting said surgical instrument and said clamping means with the output of said pneumatic control unit for simultaneously providing pneumatic pressure pluses to said surgical instrument and said clamping means, whereby said surgical instrument and said clamping means are simultaneously actuated and simultaneously deactuated, said clamping means thereby functioning to prevent negative pressure from being applied through said collapsible conduit to the surgical instrument in the absence of pneumatic pressure pulses from said control unit for operating the surgical instrument.

2. The surgical apparatus of claim 1 wherein said clamping means includes a reciprocating clamping member and a clamping wall, and said section of said conduit is disposed between said reciprocating member and said clamping wall.

3. The surgical apparatus of claim 2 wherein said reciprocating clamping member includes an orthogonal edge, and said conduit is disposed between said orthogonal edge, and said clamping wall.

4. A surgical apparatus comprising:
   (a) a powered intraocular surgical instrument of the type which is actuated by a series of pneumatic pressure pulses;
   (b) a pneumatic control unit for providing a series of pneumatic pressure pulses to actuate said surgical instrument;
   (c) a receptacle for receiving material evacuated from said surgical instrument, said receptacle including a pneumatic connection means for pneumatically connecting the interior of said receptacle to a source of negative pressure;
   (d) a collapsible conduit fluidly connecting said surgical instrument with the interior of said receptacle for evacuating material from said surgical instrument by pneumatically conducting negative pressure from the inside of said receptacle to said surgical instrument;
   (e) a pneumatically operated clamping means which is effective when deactuated to cut off the application of negative pressure through said collapsible conduit and to contract the interior volume of said conduit between said clamping means and said instrument to dissipate residual negative pressure existing therebetween by clamping a section of said collapsible conduit, and which is effective when actuated by a pneumatic pressure pulse to unclamp said section of said conduit and thereby to permit negative pressure to be applied through said conduit; and
   (f) a pneumatic connection means fluidly connecting said surgical instrument and said clamping means with the output of said pneumatic control unit for simultaneously providing pneumatic pulses to said surgical instrument and said clamping means, whereby said surgical instrument and said clamping means are simultaneously actuated and simultaneously deactuated, said clamping means thereby functioning to prevent negative pressure from being applied through said collapsible conduit to the surgical instrument in the absence of pneumatic pressure pulses from said control unit for operating the surgical instrument.

5. The surgical apparatus of claim 4 wherein said clamping means includes a reciprocating clamping member and a clamping wall, and said section of said collapsible conduit is disposed between said reciprocating clamping member and said clamping wall.

6. The surgical apparatus of claim 5 wherein said reciprocating clamping members includes an orthogonal edge, and said section of said conduit is disposed between said edge and said clamping wall.

7. The surgical apparatus of claim 6 wherein said receptacle further includes an adjustable pressure valve means for adjusting and maintaining negative pressure within the interior of said receptacle to a selected value.

8. The surgical apparatus of claims 4, 5, 6 or 7 wherein said receptacle further includes a vacuum gauge for measuring and displaying the value of the negative pressure therein.

9. A process for controlling the aspiration and evacuation of an intraocular surgical instrument actuated by a series of pneumatic pressure pulses provided by a pneumatic control unit, comprising the steps of:

(a) fluidly connecting one end of a collapsible aspirating and evacuating conduit to the intraocular surgical instrument and the other end of said conduit to a source of negative pressure;

(b) placing a section of said conduit into operative association with a pneumatically actuated clamping device, said clamping device being effective to clamp shut said section of said conduit when the clamping device is deactuated and to unclamp said section of said conduit when the clamping device is actuated by a pneumatic pressure pulse;

(c) fluidly connecting both the surgical instrument and the clamping means to the output of the pneumatic control unit; and (d) operating said pneumatic control unit to deliver simultaneous pneumatic pressure pulses to the intraocular surgical instrument and to the clamping device, whereby the intraocular surgical instrument and the clamping device are simultaneously actuated and simultaneously deactuated, said clamping device thereby functioning to prevent negative pressure from being applied through said collapsible conduit to the surgical instrument in the absence of pneumatic pressure pulses from said control unit for operating the surgical instrument.

10. The process of claim 9 wherein the clamping device includes a reciprocating member having an orthogonal edge, and a clamping wall, and wherein said section of said conduit is disposed between said orthogonal edge and said clamping wall.

* * * * *